United States Patent [19]

Spada et al.

[11] Patent Number: Plant 5,344

[45] Date of Patent: Nov. 20, 1984

[54] PEACH TREE

[75] Inventors: Aldo Spada; Emidio Palombi, both of Tarquinia, Italy

[73] Assignee: Superior Farming Company, Bakerside, Calif.

[21] Appl. No.: 469,566

[22] Filed: Feb. 24, 1983

[51] Int. Cl.[3] ..... A01H 5/03

[52] U.S. Cl. ..... Plt./43

[58] Field of Search ..... Plt./43

*Primary Examiner*—Robert E. Bagwill

*Attorney, Agent, or Firm*—Synnestvedt & Lechner

[57] ABSTRACT

A peach tree ripening 13–16 days earlier than the parent variety, Springcrest.

5 Drawing Figures

This invention relates to the discovery and asexual reproduction of a new and distinct variety of peach tree cv. S. Isidoro/A.S. 75. The new variety is a sport of the "Springcrest" variety of peach tree (unpatented).

The new variety was discovered by Aldo Spada on the S. Isidoro farm in Portaccia, new Taraquinia, Italy, and was first propagated by Emidio Palombi, also in Portaccia, near Taraquinia, Italy, where he asexually reproduced it by budding to peach seedling rootstock of the prunus persica silvestres variety. Subsequent reproduction of the plant by budding was conducted at the S. Isidoro farm at Portaccia have shown that the sport is stable in its essential characteristics and holds its distinguishing characteristics through successive propagations.

The characteristics of the new peach S. Isidoro/A.S. 75 are substantially identical to those of the parent Springcrest peach and to two other sports of the Springcrest peach—the Maycrest peach (U.S. Plant Pat. No. 4,064) and the Morning Sun peach (U.S. Plant Pat. No. 4,827) except that the S. Isidoro/A.S. 75 peach ripens 13–16 days earlier than the Springcrest peach and 7–10 days earlier than the Maycrest peach and the Morning Sun peach. In addition, the suture of the S. Isidoro/A.S. 75 peach is more pronounced than the suture of the Springcrest peach.

Figure 1:
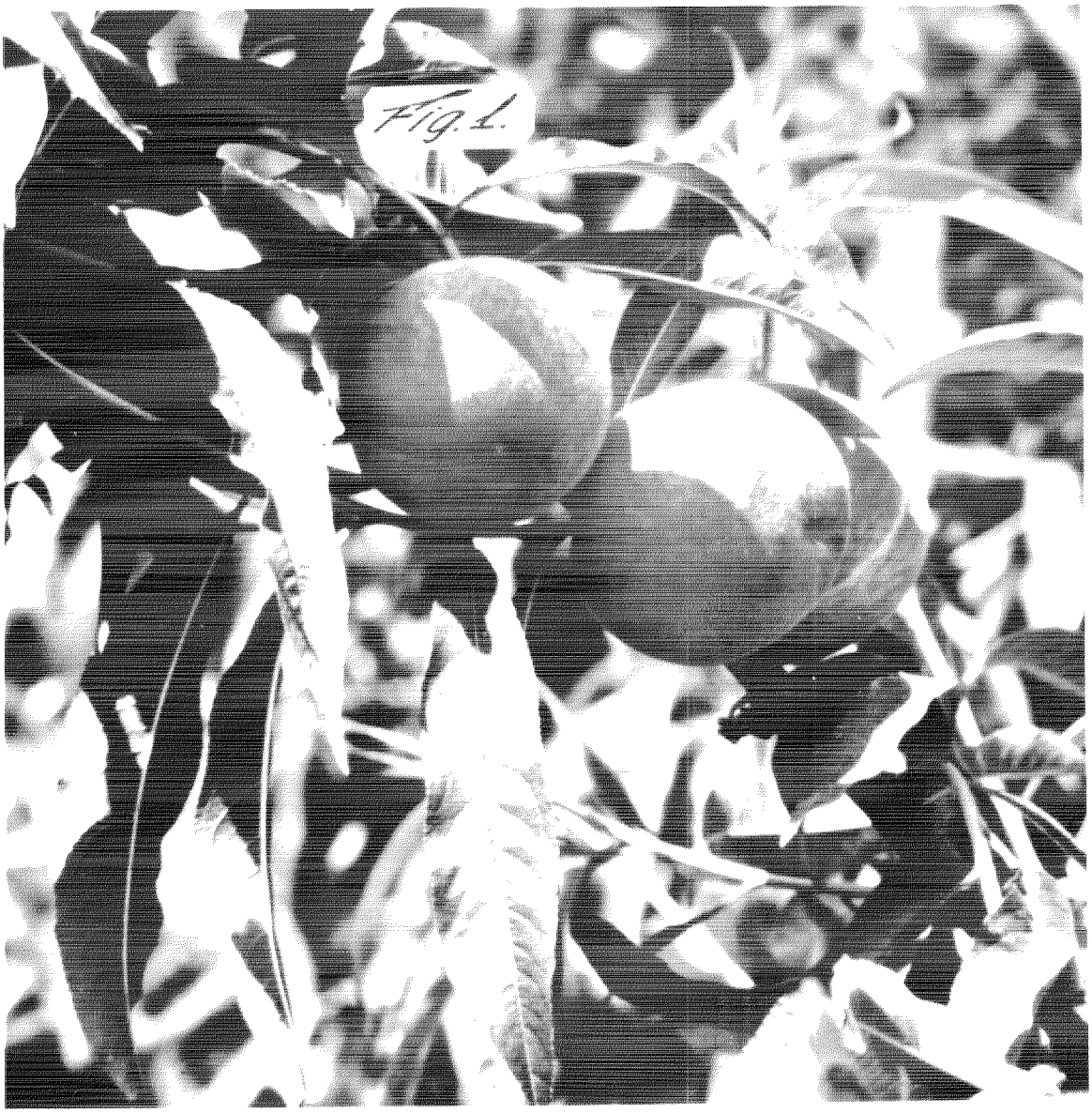

In the accompanying drawings, on Sheet 1, FIG. 1 is a full color photograph of a portion of branch of the S. Isidoro/A.S. 75 peach tree growing on the S. Isidoro farm and shows typical foliage and bearing fruit approaching maturity.

Sheet 2 is a colored photo of mature fruit of the S. Isidoro/A.S. 75 peach.

Figures 2A, 2B, 2C, 2D:
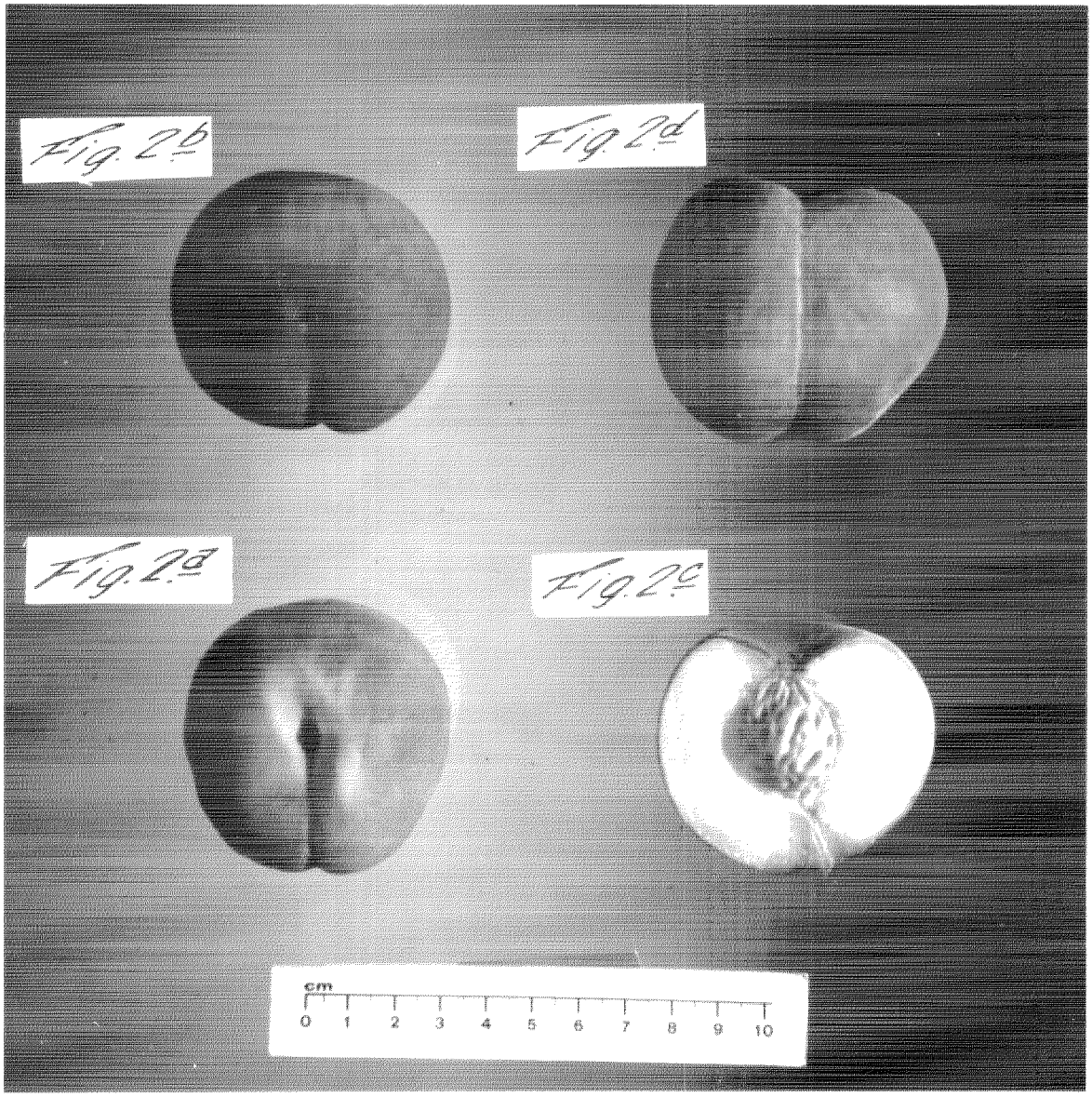

FIG. 2*a* shows the peach viewed from the apex or stem end.

FIG. 2*b* shows the peach viewed from the base.

FIG. 2*c* shows the peach cut in half on a plane generally perpendicular to the suture plane and with the stone exposed and in place.

FIG. 2*d* shows a side view of the peach looking at the suture line.

In the description that follows, and which relates to a tree of the new variety grown near Taraquinia, Italy, color designations beginning with a small letter are used when the name of that color, as used in common speech, is aptly descriptive. Color designations beginning with capital letters represent values based on the R.H.S. Colour Chart put out by The Royal Horticultural Society, London, England; color designations preceeded by "BBC" refer to the colours of the British Colour Council (Ridgeway Repertoire Ostwald) charts.

TREE

The tree is of medium size, of upright-spreading habit, and of moderately vigorous growth. Its foliage is open, and vase-form. It is a half-hardy tree, and in the Taraquinia area, it is productive and bears regularly. The trunk is stocky and of medium size and has a smooth to medium texture. Its branches are of medium caliper, and are smooth to medium texture. They are smooth in texture, and their color varies from near Yellow Green 144B (BCC Scheeles Green 860/3) on one side and to near Greyed-Purple 186A (BCC Chrysanthemum Crimson 824/1) on the opposite side. There are a medium number of medium to small size lenticels.

LEAVES

The leaves are of medium thickness and large in size, averaging about 182 mm in length and about 40 mm in width. The form is lanceolate, with apex acuminate. The color of the topside is near Yellow-Green 147A (i.e., equivalent to BCC Leek Green 000858) and near between Yellow-Green 152A to 152B (i.e., the equivalent of BCC Lavender Green 000761/1 to 000761) on the underside. The leaf surface is smooth in texture, and the leaf margins are coarsely serrate and somewhat undulate. The petiole is of medium length and thickness and averages about 1.2 mm. There are usually 2, and sometimes 3, but seldom 1 or 4, small size (about 1 mm), globose glands, on the petiole and base of the leaf. The glands are generally oppositely arranged but sometimes alternately arranged. There are no stipules.

BUDS AND FLOWERS

The flower buds are near Yellow-Green 147A (BCC Leek Green 000858) in color, pubescent, obtuse in shape and medium in size. Their hardiness ranges from hardy to half-hardy.

The flowers come into first bloom about March 4 and into full bloom by March 11 in Taraquinia, which is the same as the Springcrest but early in comparison with other peaches in the neighborhood. The blossoms are large. The flowers are near Red 56A (BBC Pink 623/3) in color.

FRUIT

The mature fruit is of uniform, medium size. The date of the first picking was May 25 and the last picking was June 2. The axial diameter is from 55 to 60 mm; the diameter transverse the suture plane from 55 to 60 mm; and the diameter at right angles to the suture plane, from 55 to 60 mm. The fruit is uniformly globose.

The suture extends from base to apex and is of slight to medium in depth and there is a slight depression beyond the pistil point.

The ventral surfaces are slightly rounded and the lips genérally equal.

Stem and stem cavity: The stem cavity is rounded about 10 mm in depth and 30 mm in breadth. The base is rounded. The apex is rounded to truncate and depressed. The pistil point is pronounced.

The stem is about 10 mm in length, of medium caliper (average — about 3 mm) and glabrous. It manifests medium adherence to the stone.

Skin: The skin is of thin to medium thickness. It is tough and tenacious to the flesh. It manifests no tendency to crack in a wet or dry season. Its ground color is near Yellow-Orange 21B and blushes over 70–90 percent of the surface to Red 43A. The down is short, scant and does not roll up when rubbed.

EATING QUALITY OF FRUIT

This description refers to a peach which was ripe when picked in this case between May 25 and June 2.

FLESH

The flesh is between Yellow 8C and Yellow 8D in color.

The juice is abundant to moderate.

The texture is firm.

The fibres were few.

The fruit ripens evenly. Its flavor is delicate. The aroma was not pronounced. The eating quality is good.

STONE

The stone is semi-free. It has short fibres. The stone adheres to the flesh over the upper half of sides and has long fibres. The stone is small in size, being an average length of about 26 mm and an average breadth of about 21 mm and its average thickness runs about 16 mm. The form of the stone is ovoid in form. The base is oblique; the hilum narrow. The apex is acute. The sides are equal and the surface is irregularly furrowed throughout. The ridges are rounded toward the apex. The ridges are jagged, toward the base and apex.

The ventral edge is thin, and is with wing throughout.

The dorsal edge is broadly grooved throughout; toward the base. There is only a slight tendency to split in wet seasons and no tendency to split in dry seasons.

The color of the stone is between Yellow-Orange 23C to Yellow-Orange 23D.

The fruit has good keeping and shipping qualities.

The variety has medium resistance to insects and to diseases.

We claim:

1. A new and distinct variety of peach tree as a sport of the peach tree cv. Springcrest (unpatented) characterized in that it ripens 13 to 16 days earlier than the Springcrest peach and shows a more pronounced suture than that of the Springcrest peach.

* * * * * cm
0 1 2 3 4 5 6 7 8 9 10